US006746121B2

(12) United States Patent
Ross et al.

(10) Patent No.: US 6,746,121 B2
(45) Date of Patent: Jun. 8, 2004

(54) DEFOCUS AND ASTIGMATISM COMPENSATION IN A WAVEFRONT ABERRATION MEASUREMENT SYSTEM

(76) Inventors: Denwood F. Ross, 8420 Center Road South, Austinburg, OH (US) 44010; Michael Schottner, Richard-Wagner Strasse 20, Leiman (DE), D-69181; Bjorne Baschek, Adfalbert-Seifriz Strasse 25, Neckargemuend D-69151 (DE); Josef Bille, Hermann-Loens-Weg 44/1, Heidelberg (DE), D-69118

( * ) Notice: Subject to any disclaimer, the term of this patent is extended or adjusted under 35 U.S.C. 154(b) by 0 days.

(21) Appl. No.: 09/844,930

(22) Filed: Apr. 27, 2001

(65) Prior Publication Data
US 2002/0159029 A1 Oct. 31, 2002

(51) Int. Cl.[7] ............................................. A61B 3/10
(52) U.S. Cl. ....................................................... 351/212
(58) Field of Search .................................. 351/211, 212, 351/222, 216, 221, 246; 359/641, 642, 618

(56) References Cited

U.S. PATENT DOCUMENTS

| 3,822,932 A | * | 7/1974  | Humphrey ............... 351/222 |
| 3,969,020 A | * | 7/1976  | Lynn et al. |
| 4,422,735 A | * | 12/1983 | Shimizu et al. |
| 5,420,651 A | * | 5/1995  | Kamppeter |
| 6,042,232 A | * | 3/2000  | Luce et al. |
| 6,095,651 A | * | 8/2000  | Williams et al. |
| 6,264,328 B1 | * | 7/2001 | Williams et al. ............ 351/221 |
| 6,400,513 B1 | * | 6/2002 | Southwell .................... 359/641 |

FOREIGN PATENT DOCUMENTS

| WO | WO 01 28410 A1 | * | 4/2001 |
| WO | WO 01 28411 A1 | * | 4/2001 |

OTHER PUBLICATIONS

Communication Relating to the Results of the Partial Search Report for Application No. PCT/US02/13420 dated Sept. 20, 2002.*

* cited by examiner

Primary Examiner—George Manuel
(74) Attorney, Agent, or Firm—Lois A. Gianneschi

(57) ABSTRACT

Defocus and astigmatism compensation methods and apparatuses for use in an aberration measurement system. The apparatuses including reflectors for altering the optical distance between a pair of lenses passing a wavefront without changing the physical distance between the lenses, thereby compensating for defocus in the wavefront; and cylindrical mirrors for adding and removing curvature from a curved wavefront, thereby compensating for astigmatism in the wavefront. The methods including passing a wavefront having defocus through a first lens on a first path, reflecting the wavefront from the first path to a second path, reflecting the wavefront from the second path to a third path, and passing the wavefront through a second lens as a defocus compensated wavefront; and passing a wavefront through first and second cylindrical lens, and orienting the first and second cylindrical lenses with respect to the wavefront and to one another to compensate for astigmatism in the wavefront.

25 Claims, 7 Drawing Sheets

DEFOCUS AND ASTIGMATISM COMPENSATION IN A WAVEFRONT ABERRATION MEASUREMENT SYSTEM

FIELD OF THE INVENTION

The present invention relates generally to optical instruments and, more particularly, to a method and device for defocus and astigmatism compensation in wavefront aberration measurement systems. The present invention is particularly useful, but not exclusively so, for defocus and astigmatism compensation in ophthalmic applications.

BACKGROUND OF THE INVENTION

The human eye is an optical system employing several lens elements to focus light rays representing images onto the retina within the eye. The sharpness of the images produced on the retina is a factor in determining the visual acuity of the eye. Imperfections within the lens and other components and material within the eye, however, may cause the light rays to deviate from the desired path. These deviations, referred to as aberrations, result in blurred images and decreased visual acuity. Hence, methods and apparatuses for measuring aberrations are desirable to aid in the correction of such problems.

One method of detecting aberrations introduced by the eye involves determining the aberrations of light rays exiting from the eye. A beam of light directed into the eye as a point on the retina is reflected or scattered back out of the eye as a wavefront, with the wavefront containing aberrations introduced by the eye. By determining the propagation direction of discrete portions (i.e., samples) of the wavefront, the aberrations introduced by the eye can be determined and corrected.

A general illustration of the generation of a wavefront is shown in FIG. 1. FIG. 1 is a schematic view of a wavefront 10 generated by reflecting a laser beam 12 off of the retina 14 of an eye 16. The laser beam 12 focuses to a small spot 18 on the retina 14. The retina 14, acting as a diffuse reflector, reflects the laser beam 12, resulting in the point source wavefront 10. Ideally, the wavefront 10 would be represented by a planar wavefront 20. However, aberrations introduced by the eye 16 as the wavefront 10 passes out of the eye 16 result in an imperfect wavefront, as illustrated by the aberrated wavefront 20A. The wavefront 10 represents aberrations which lead to defocus, astigmatism, spherical aberrations, coma, and other irregularities. Measuring and correcting these aberrations allow the eye 16 to approach its full potential, i.e., the limits of visual resolution.

FIG. 2 is an illustration of a prior art apparatus for measuring the wavefront 10 as illustrated in FIG. 1. By measuring the aberrations, corrective lenses can be produced and/or corrective procedures performed to improve vision. In FIG. 2, a laser 22 generates the laser beam 12 which is routed to the eye 16 by a beam splitter 24. The laser beam 12 forms a spot 18 on the retina 14 of the eye 16. The retina 14 reflects the light from the spot 18 to create a point source wavefront 10 which becomes aberrated as it passes through the lens and other components and materials within the eye 16. The wavefront 10 then passes through a first lens 11 and a second lens 13 to focus the wavefront 10 so that the wavefront 10 is collimated. The wavefront 10 then passes through the beam splitter 24 toward a wavefront sensor 26. Information detected by the wavefront sensor 26 is then processed by a processor 27 to determine the aberrations of the wavefront 10.

FIG. 3 illustrates the focusing of the wavefront 10 to produce a flat wavefront for projection onto the wavefront sensor 26. If the wavefront 10 contains diverging light, the light rays which make up the wavefront 10 would continue to diverge until they were no longer contained within the system, thereby losing valuable wavefront 10 information. This is especially problematic for an eye 16 having a large degree of defocus. In FIG. 3 the curved wavefront 10A containing diverging light rays passes through the first lens 11 where it converges to a crossover point 15, and then through the second lens 13. When the crossover point 15 occurs at one focal length before the second lens 13, the resultant wavefront 10B will be collimated (i.e., flat). For different degrees of defocus, the lenses 11 and 13 can be moved relative to one another in order for the focal point of lens 13 to match the cross-over point 15. Unfortunately, for an eye 16 having a great deal of defocus, the lenses 11 and 13 may need to be moved a relatively large distance from one another, which may be problematic if space is limited. In addition, the defocus mechanism of FIG. 3 does not correct other eye aberrations such as astigmatism in which light along one axis converges/diverges more rapidly than light along another axis. Since the lenses 11 and 13 converge or diverge light along every axis equally, this arrangement does not compensate for astigmatism.

Typical wavefront sensors 26 include either an aberroscope 28 (FIG. 4) or a Hartman-Shack lenslet array 30 (FIG. 5), with an imaging device 32. The aberroscope 28 and the Hartman-Shack lenslet array 30 each produce an array of spots when a wavefront passes through them. The imaging device 32 contains an imaging plane 34 for capturing the spots generated by the aberroscope 28 or the Hartman-Shack Sensor 30. Generally, the imaging device 32 is a charge coupled device (CCD) camera.

The wavefront sensor 26 samples the wavefront 10 by passing the wavefront 10 through the aberroscope 28 or the Hartman-Shack sensor 30, resulting in an array of spots on the imaging plane 34. Each spot on the imaging plane 34 represents a portion of the wavefront 10, with smaller portions enabling the aberrations to be determined with greater accuracy. By comparing the array of spots produced on the imaging plane 34 by the wavefront 10 with a reference array of spots corresponding to the wavefront of an ideal eye, the aberrations introduced by the eye 16 can be computed.

An example of a Hartman-Shack system is described in U.S. Pat. No. 6,095,651 to Williams et al., entitled Method and Apparatus for Improving Vision and the Resolution of Retinal Images, filed on Jul. 2, 1999, is incorporated herein by reference.

The resolution of the aberrations in such prior art devices, however, is limited by the sub-aperture spacing 36 and the sub-aperture size 38 in an aberroscope sensor (see FIG. 4), and by the lenslet sub-aperture size 40 and focal length in a Hartman-Shack sensor (see FIG. 5). In addition, large aberrations due to excessive defocus or astigmatism may result in foldover. Foldover occurs in an aberroscope sensor, for example, when two or more spots 42A, 42B, and 42C on the imaging plane 34 overlap, thereby leading to confusion between adjacent sub-aperture spots. Similarly, foldover occurs in Hartman-Shack sensors when two or more spots 44A, 44B, 44C, and 44D on the imaging plane 34 overlap. Typical systems are designed to accommodate a certain amount of defocus and astigmatism, however, these systems are unable to handle defocus and astigmatism of individuals with large astigmatism and/or large defocus.

Foldover may result from a sub-aperture spacing 36, sub-aperture size 38, or lenslet size 40 which is too small, a high degree of aberration (e.g., large defocus and/or astigmatism); or a combination of these conditions. Hence, the sub-aperture spacing 36 and sub-aperture size 38 in the aberroscope sensor (FIG. 4), and the lenslet sub-aperture spacing 40 and focal length in the Hartman-Shack sensor (FIG. 5) must be selected to achieve good spatial resolution while enabling the measurement of large aberrations. Accordingly, the ability to measure a high degree of aberration comes at the expense of spatial resolution and/or dynamic range and vice versa.

The constraints imposed by the aberroscope and Hartman-Shack approaches limit the effectiveness of these systems for measuring wavefronts having a wide range of aberrations, such as those exhibiting a large degree of defocus and astigmatism. These limitations prevent existing optical systems from achieving their full potential. Accordingly, ophthalmic devices and methods which can measure a wide range of aberrations having of defocus and/or astigmatism with a high degree of accuracy would be useful.

SUMMARY OF THE INVENTION

The present invention provides for a method and apparatus of compensating for defocus and astigmatism in a wavefront for use in an ophthalmic system for measuring eye aberrations. By compensating for at least a portion of defocus and astigmatism, the method and apparatus of the present invention are capable of measuring a wide range of aberrations in a wavefront with a high degree of accuracy.

In an ophthalmic system for measuring eye aberrations having first and second optical lenses separated by a physical distance for focusing a wavefront, the present invention includes a method of adjusting the optical distance between the two lenses without changing the physical distance between the two lenses. The method of the present invention includes passing a wavefront through a first optical lens in a first optical path, reflecting the wavefront from the first optical path to a second optical path, reflecting the wavefront to a third optical path, and passing the wavefront through a second optical lens. In addition, the method may include reflecting the wavefront to a fourth optical path after being reflected to the third optical path and before being passed through the second optical lens. The reflections allow the optical distance between the first and second optical lenses, and therefore the defocus compensation, to be changed without altering the physical distance between the lenses. Also, the reflections allow incremental changes in certain components to result in larger incremental changes in the optical distance between the lenses, thereby allowing a larger range of defocus compensation to be performed in a smaller physical area.

Another method of the present invention includes passing a wavefront through a cylindrical lens assembly to remove astigmatism from the wavefront. The method includes passing the wavefront through a first cylindrical lens and a second cylindrical lens, orienting the first cylindrical lens and the second cylindrical lens such that an astigmatism compensation position of the cylindrical lens assembly is in-line with a bisector position of the wavefront, and orienting the first and second cylindrical lenses relative to one another to adjust the astigmatism compensation power of the cylindrical lenses to compensate for astigmatism in the wavefront.

An apparatus of the present invention for changing the optical distance traveled by a wavefront between a pair of lenses without changing the physical distance between the lenses includes a first reflector positioned to reflect the wavefront received from a first lens along a first optical path to a second optical path, a second reflector positioned to reflect the wavefront from the second optical path to a third optical path, and a third reflector positioned to reflect the wavefront from the third optical path to a fourth optical path which passes through a second optical lens.

An apparatus of the present invention for compensating for astigmatism includes a first cylindrical lens for introducing a first cylindrical refraction to a wavefront, a second cylindrical lens for introducing a second cylindrical refraction to the wavefront, and a support for rotatably mounting the first and second cylindrical lenses, the first and second cylindrical lenses being rotatable relative to the wavefront and relative to one another, whereby an astigmatism within the wavefront is compensated by adjusting the orientation of the first cylindrical lens and the second cylindrical lens relative to the wavefront and to one another.

DETAILED DESCRIPTION OF THE INVENTION

Figure 1:
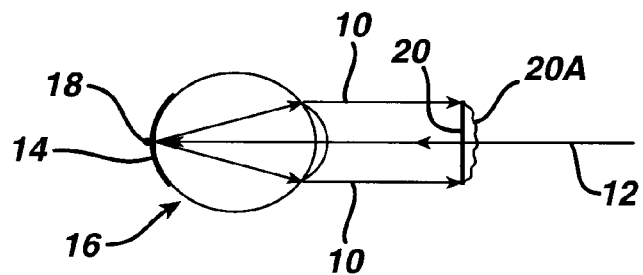
FIG. 1 is a schematic of a wave produced by a laser beam reflected by the retina of an eye.
Figure 2:
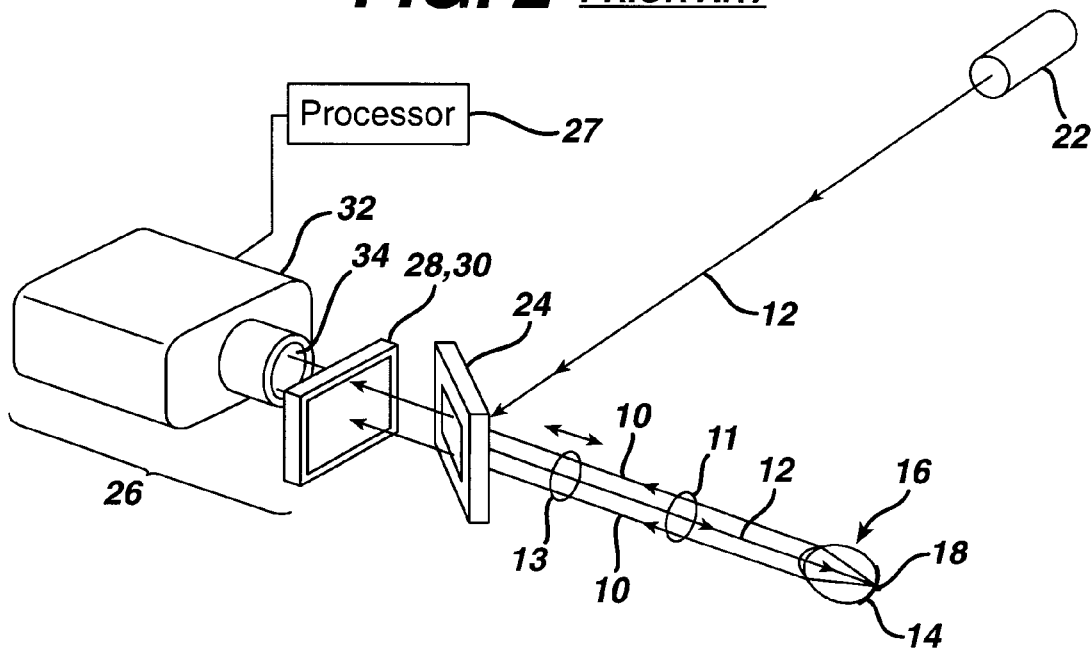
FIG. 2 is a schematic of a prior art apparatus for measuring aberrations introduced by an eye.
Figure 3:
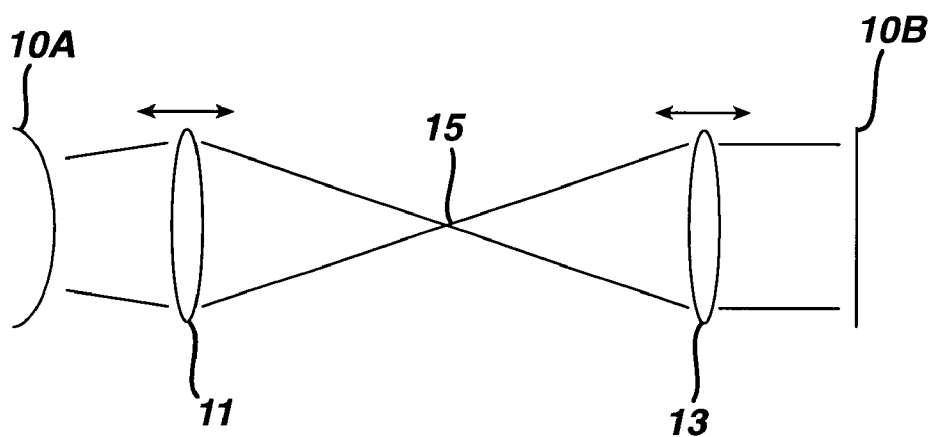
FIG. 3 is a schematic of a part of a prior art defocus compensation device.
Figure 4:
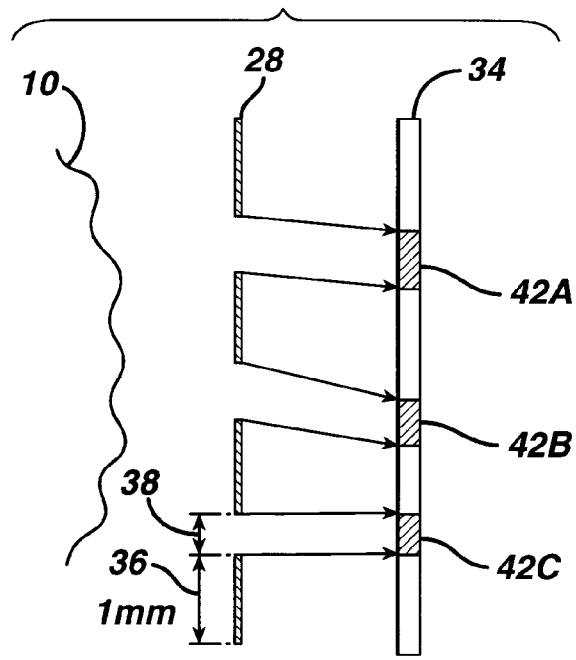
FIG. 4 is a schematic of an aberroscope system for use in a prior art apparatus for measuring aberrations.
Figure 5:
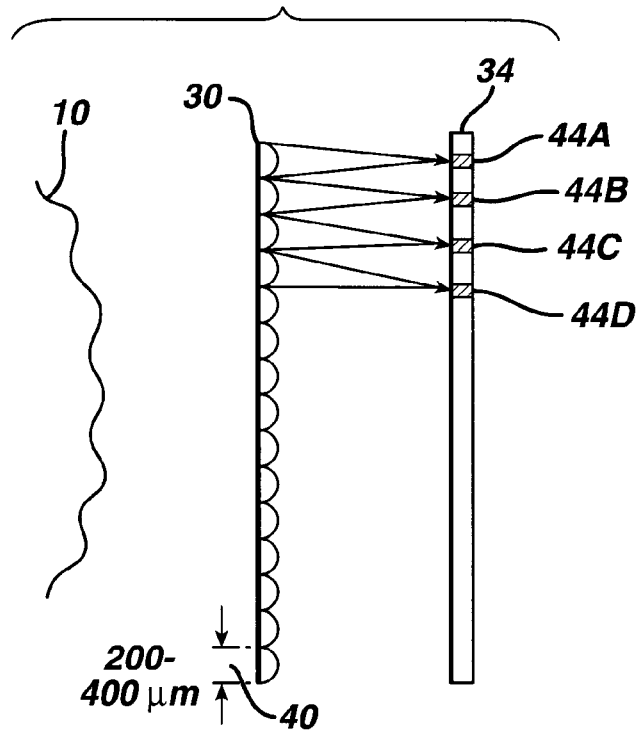
FIG. 5 is a schematic of a Hartman-Shack lenslet array system for use in a prior art apparatus for measuring aberrations.
Figure 6:
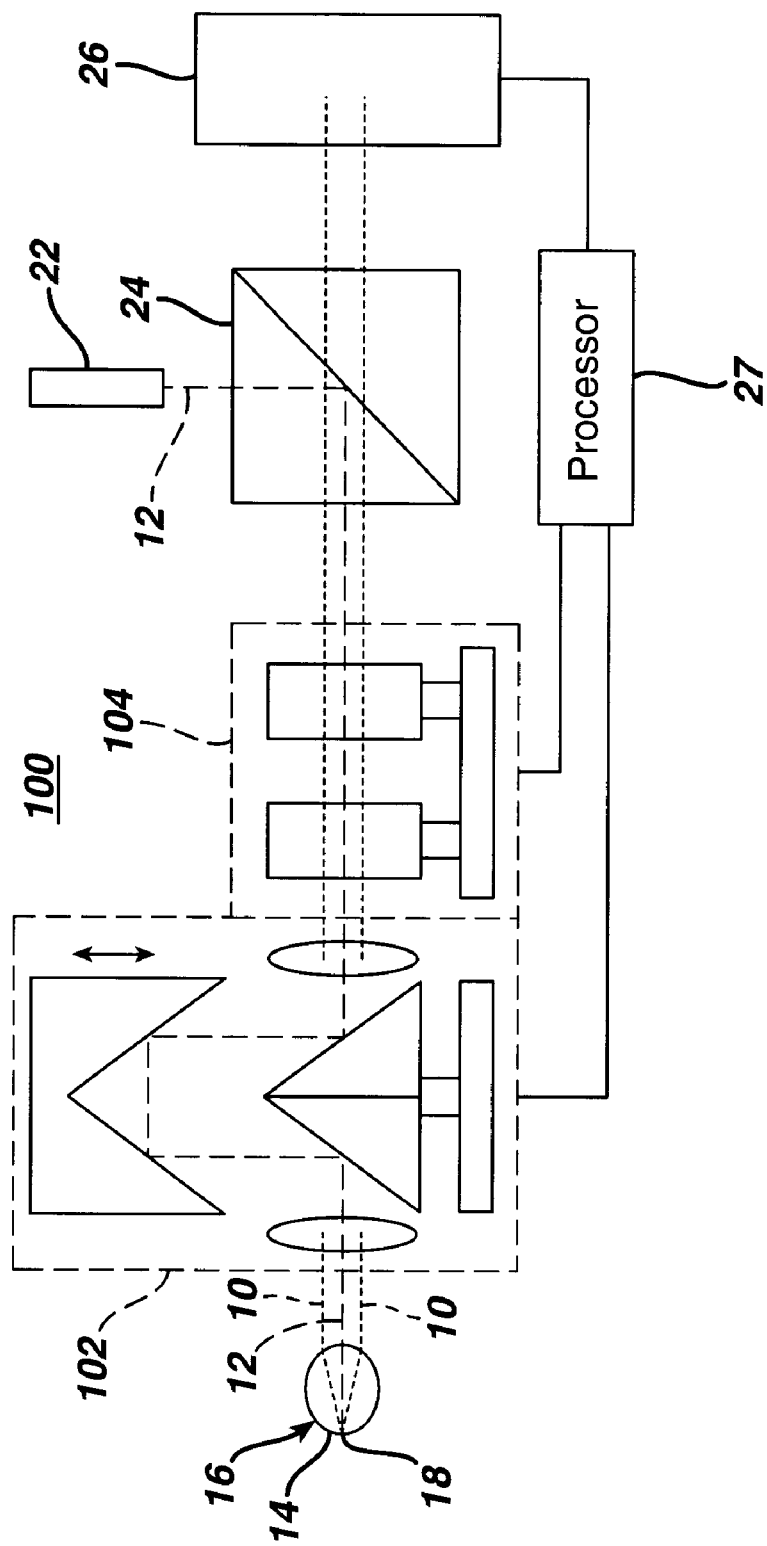
FIG. 6 is a schematic of an apparatus for measuring aberrations in a wavefront introduced by an optical system in accordance with the present invention.

Illustrated in FIG. 6 is a preferred embodiment of a wavefront measuring apparatus 100 for measuring the aberrations of an eye 16 in accordance with the present invention. In a general overview, a beam 12 is generated by a laser 22 and directed by a beam splitter 24 into the eye 16. The diameter of the beam 12 is small, thereby minimizing the effect of optical components between the laser 22 and the eye 16 on the beam 12. A wavefront 10 is reflected out of the eye toward a wavefront sensor 26 for measurement of aberrations introduced to the wavefront 10 by the eye 16.

If the wavefront 10 contains a relatively large amount of defocus or astigmatism, portions of the wavefront 10 may not reach the wavefront sensor 26 or may be out of range for measurement by the wavefront sensor 26. Therefore, the wavefront 10 is passed through a novel defocus compensation device 102 and through a novel astigmatism compensation device 104 to compensate for relatively large defocus and astigmatism, respectively, within the wavefront 10.

The defocus compensation device 102 adds a defocus compensation component to the wavefront 10, and the astigmatism compensation device 104 adds an astigmatism compensation component to the wavefront 10. Remaining aberrations within the wavefront 10, after defocus and astigmatism compensation, are then detected by the wavefront sensor 26. The processor 27 then determines the aberrations of the wavefront 10 based of the information obtained from the wavefront sensor 26, the defocus compensation component added by the defocus compensation device 102, and the astigmatism compensation component added by the astigmatism compensation device 104.

By compensating for defocus and astigmatism prior to measurement by the wavefront sensor 26, the wavefront sensor 26 can be configured to detect the remaining aberrations more precisely. In addition, the wavefront measuring apparatus 100 is able to detect a wider range of aberrations since defocus and astigmatism aberrations, which were previously out of the wavefront sensor's range, are compensated for by the defocus compensation device 102 and the astigmatism compensation device 104 with the compensation components of these devices factored into the determination of the aberrations of the wavefront 10.

In the present invention, the generation of the beam 12 and the wavefront 10, and the determination of aberrations of the wavefront 10 by the processor 27 are known in the art. In addition, modifications to processor 27 to factor in the defocus compensation component and the astigmatism compensation component in determining the aberrations of the wavefront 10 will be readily apparent to those in the art. The defocus compensation and astigmatism compensation of the present invention are now described in more detail.

Defocus Compensation

Figure 7:
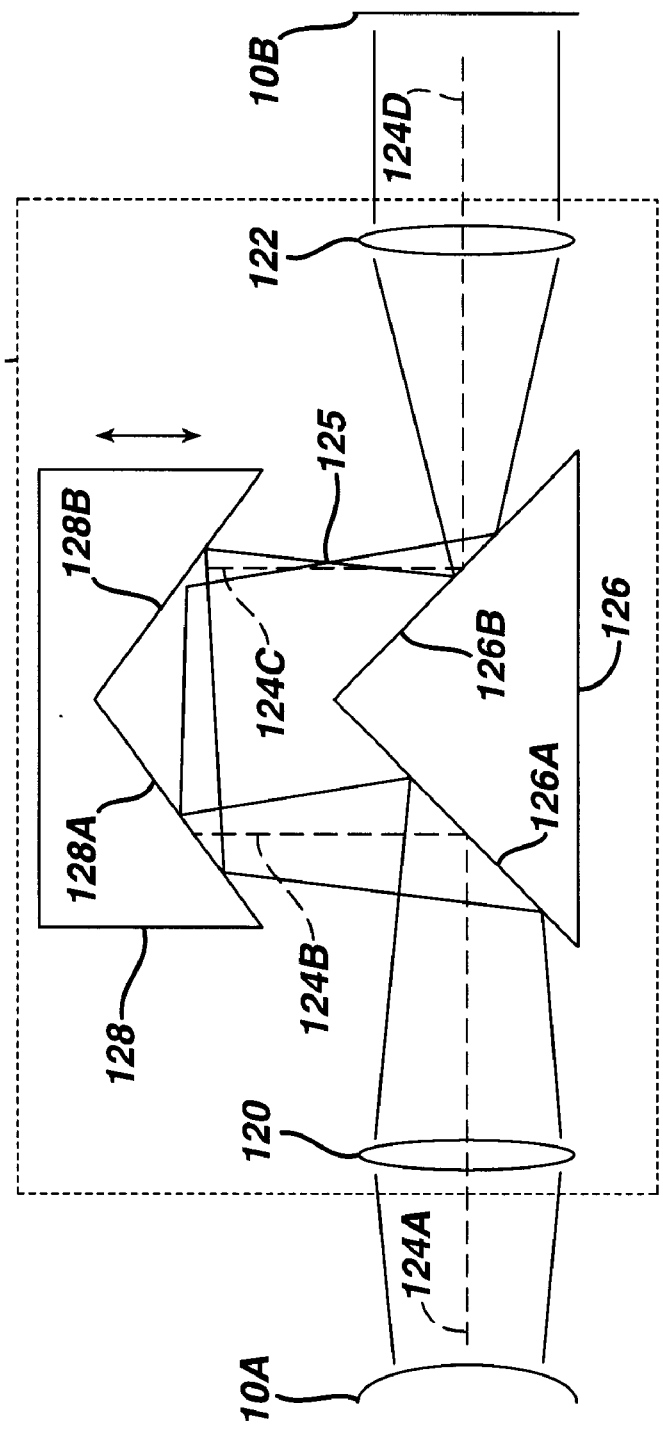
FIG. 7 is an illustrative schematic of a defocus compensation device for removing a defocus component from a wavefront for use in the apparatus of FIG. 6 in accordance with the present invention.

FIG. 7 illustrates a preferred defocus compensation device 102 in accordance with the present invention. The defocus compensation device 102 includes a first and second lens 120 and 122 to compensate for defocus in a wavefront (a wavefront containing defocus is represented by curved wavefront 10A) and generate a defocus compensated wavefront (represented by flat wavefront 10B) for measurement by a wavefront sensor 26 (FIG. 6). The defocus compensation device 102 removes at least a portion of defocus within the wavefront such that the remaining defocus within the wavefront is measurable by the wavefront sensor 26. The wavefront sensor may then be configured to detect the remaining defocus more precisely. The amount of defocus compensated for by the defocus compensation device 102 and the defocus determined by the wavefront sensor 26 may then be combined by the processor 27 to determine the aberrations of the eye 16 (FIG. 6) due to the total defocus.

A first lens 120 of the defocus compensation device 102 is a spherical lens for focusing the wavefront 10 (FIG. 6). The wavefront 10 passes through the lens 120 along a first optical path 124A. The lens 120 focuses the diverging light of the curved wavefront 10A to a cross-over point 125.

A first reflector 126A reflects the wavefront 10 from the first optical path 124A to a second optical path 124B which is different from the first optical path 124A. In the preferred embodiment, the first reflector 126A is a surface of a prism 126. Other reflectors may be used, such as a mirror.

A second reflector 128 reflects the wavefront 10 to a third optical path 124C which is different from the first optical path 124A and the second optical path 124B. The second reflector 128 is preferably a retroreflector. In a retroreflector, an incoming beam such as the wavefront on the second optical path 124B will be reflected parallel to itself but in the opposite direction of propagation (e.g., optical path 124C), regardless of the orientation of the wavefront 10 with respect to the retroreflector. The retroreflector may be a corner cube or other well known retroreflector. An alternative embodiment may include a porro reflector or at least two reflective surfaces. For example, the reflector 128 may include a first reflective surface 128A, e.g., a mirror, for reflecting the wavefront 10 on the second optical path 124B along an intermediate optical path toward a second reflective surface 128B, e.g., another mirror. The second reflective surface 128B then reflects the wavefront received along the intermediate optical path along the third optical path 124C. In a preferred embodiment, the second optical path 124B and the third optical path 124C are substantially the same physical distance.

In the illustrated embodiment, the third reflector 126B reflects the wavefront from the third optical path 124C to a fourth optical path 124D. The first optical path 124A and the fourth optical path 124D are preferably substantially colinear as shown. Here, the third reflector 126B is formed as another surface of the prism 126 forming the first reflector 126A. Alternatively, the reflector 126A and reflector 126B need not be surfaces of the same device, e.g., prism 126, but may be separate reflective surfaces.

The second lens 122 is positioned along the fourth optical path 124D through which passes the wavefront 10. If the focal point of the second lens 122 is the same as the crossover point 125, a defocus compensated wavefront 10B will be produced.

It is contemplated, although not preferred, that the second lens 122 may be positioned along the third optical path 124C. Since the second lens 122 would be positioned to receive the wavefront along the third optical path 124C, directly, the third reflector 126B could be eliminated. In addition, it is further contemplated, although not preferred, that the first lens 120 may be positioned along the second optical path 124B. Since the first lens 120 would be positioned to allow the wavefront to pass along the second optical path 124B, the first reflector 126A could be eliminated.

It is seen that while the first and second lenses 120 and 122 are separated by a physical distance for focusing a wavefront 10, the optical distance between the two lenses 120 and 122 is adjusted without changing the physical distance between the two lenses 120 and 122. This is done by changing the distance between the reflector 128 and the other reflectors 126A and 126B within the defocus compensation device 102 along the second and third optical paths 124B and 124C. By changing the distance between the reflector 128 and the other reflectors 126A and 126B, the optical distance along which a wavefront must travel between the two lenses 120 and 122 is changed without changing the physical distance between the lenses 120 and 122. Further, due to the reflection by reflector 128, a incremental changes in the distance between the reflector 128 and the other reflectors 126A and 126B results in a change in the optical distance between the lenses 120 and 122 which is twice the incremental change. The optical distance changes by twice the incremental change since changing the distance between the reflector 128 and the first and second reflectors 126A and 126B will result in an incremental change in the second optical path 124B and an incremental change in the third optical path. This permits a greater defocus compensation range for the lenses 120, 122 in a limited area.

The reflector 128 is preferably moveable with respect to the other components in the defocus compensation device 102 (i.e., reflector 126A reflector 126B, lens 120, and lens 122) to change the lengths of some of the optical paths. In an alternative embodiment, the second reflector 128 remains stationary while the other components in the defocus compensation device move to change the optical path lengths.

Astigmatism Compensation

Figure 8A:
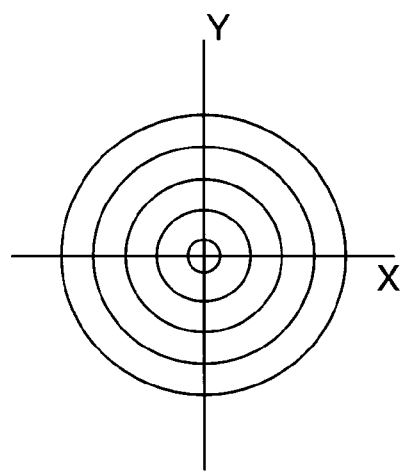
FIG. 8A is an illustrative depiction of a wavefront free of astigmatism.

FIG. 8A illustrates a wavefront pattern produced by an eye without an astigmatism. The concentric circles indicate that the eye converges light equally along every axis. An eye without an astigmatism has a single correction power (e.g., defocus) for the entire eye, which can be corrected with a lens having a single defocus correction power.

Figure 8B:
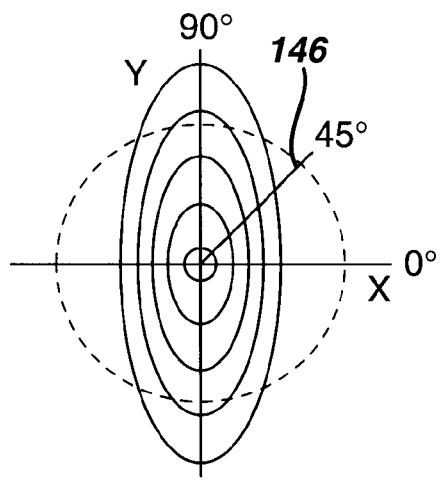
FIG. 8B is an illustrative depiction of an astigmatic wavefront.

FIG. 8B illustrates a wavefront pattern produced by an eye with an astigmatism. The concentric ovals indicate that the eye converges light more rapidly along one axis, e.g., the X axis and less rapidly along another axis, e.g., along the Y axis. In an eye with an astigmatism, the eye has essentially two powers, with an astigmatism power representing the difference between the two powers. For descriptive purposes, the line between the two powers will be referred to as the bisector position 146. The bisector position 146 lies midway between the two powers of the eye.

Figure 9:
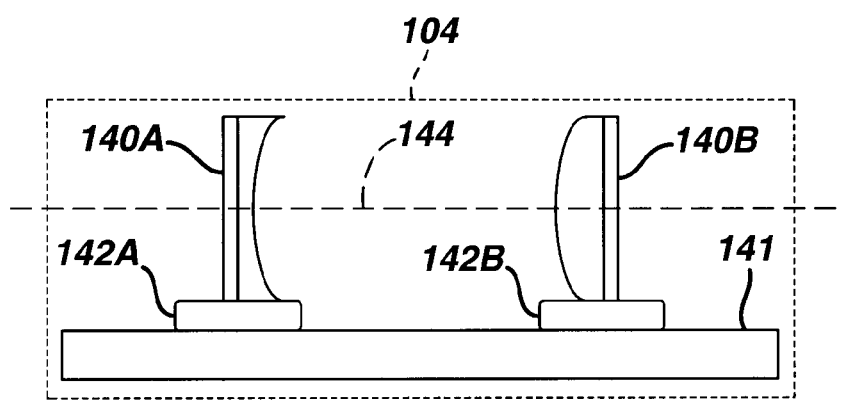
FIG. 9 is an illustrative schematic of an astigmatism compensation device for removing astigmatism component from a wavefront for use in the apparatus of FIG. 6 in accordance with the present invention.

FIG. 9 depicts a preferred astigmatism compensation device 104 for compensating for astigmatism in a wavefront 10 (FIG. 6). The astigmatism compensation device 104 is used to transform an astigmatic wavefront (represented by the concentric ovals of FIG. 8B) into a wavefront having a uniform power (represented by the concentric circles of FIG. 8A). The astigmatism compensation device 104 includes a cylindrical lens assembly having a first cylindrical lens 140A and a second cylindrical lens 140B rotatably mounted on a support 141 for selectively adding and removing curvature from the wavefront. In the illustrated astigmatism compensation device 104, the cylindrical lens 140A, 140B are rotatably mounted on a support 141 by a first rotation motor 142A and a second rotation motor 142B, respectively, for orienting the first cylindrical lens 140A and the second cylindrical lens 140B relative to the wavefront and to one another. By orienting the cylindrical lenses 140A, 140B relative to the wavefront 10 and to one another, the astigmatism within the wavefront 10 can be compensated for by removing curvature from regions having too much curvature (e.g., by diverging light along the axis having too much curvature) and adding curvature to regions having too little curvature (e.g., by converging light along the axis having too little curvature).

The astigmatism compensation device 104 removes at least a portion of astigmatism within the wavefront such that remaining astigmatism within the wavefront is measurable by the wavefront sensor 26. The wavefront sensor may then be configured to detect the remaining astigmatism more precisely. The amount of astigmatism compensated for by the astigmatism compensation device 104 and the astigmatism determined by the wavefront sensor 26 may then be combined by the processor 27 to determine the aberrations of the eye 16 (FIG. 6) due to the total astigmatism.

Figure 10A:
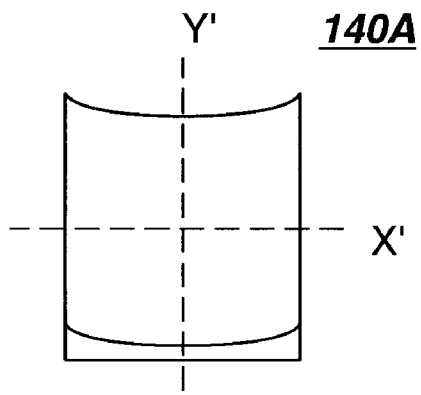
FIG. 10A is a perspective view of a concave cylindrical lens for use with the present invention.

The first cylindrical lens 140A, in the illustrated embodiment, is a diverging cylindrical lens. Preferably, the diverging cylindrical lens is a plano-concave cylindrical lens (i.e., flat on one side and curved inward on the other, see FIG. 10A). A plano-concave cylindrical lens diverges light along a curved axis, e.g., X' (FIG. 10A), thereby adding more divergence, and does not affect light along the other axis, e.g., Y' (FIG. 10A). The first cylindrical lens 140A is used to remove curvature from the regions of the wavefront 10 which are more curved, e.g., along the X axis (FIG. 8B). Preferably, the flat surface of the plano-concave cylindrical lens receives the wavefront 10 and the curved surface passes the wavefront 10.

Figure 10B:
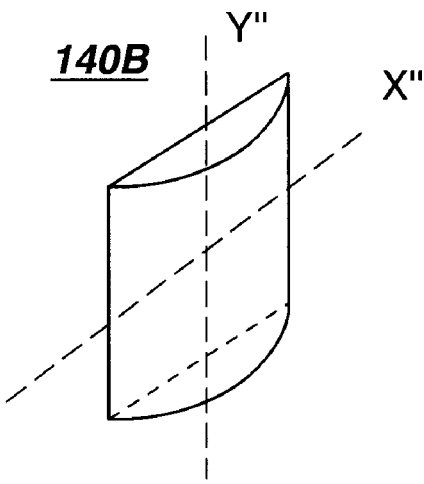
FIG. 10B is a perspective view of a convex cylindrical lens for use with the present invention.

The second cylindrical lens 140A, in the illustrated embodiment, is a plano-convex cylindrical lens (i.e., flat on one side and curved outward on the other, see FIG. 10B). A plano-convex cylindrical lens converges light along one axis, e.g., X" (FIG. 10B), thereby adding more convergence, and does not affect light along the other axis, e.g., Y" (FIG. 10B). The plano-convex cylindrical lens causes light which passes through it to converge along the curved axis. The second cylindrical lens 140B is used to add curvature to the regions of the wavefront 10 which are less curved, e.g., along the Y axis (FIG. 8B). Preferably, the curved surface of the plano-concave cylindrical lens receives the wavefront 10 and the flat surface passes the wavefront 10.

The rotation motors 142A, 142B are operably associated with the cylindrical lens 140A, 140B, respectively, for rotating its respective cylindrical lens 140A, 140B about an optical axis 144 of the wavefront 10 (FIG. 6). Suitable rotation motors for use with the present invention are readily available, with the selection of an appropriate rotation motor and its connection to a cylindrical lens 140A and 140B being apparent to those skilled in the art.

By rotating the cylindrical lenses 140A, 140B with respect to the wavefront 10, an astigmatism compensation position of the astigmatism compensation device 104 can be aligned with the bisector position 146 (FIG. 8B) of the wavefront. The astigmatism compensation position is the position midway between the flat axis of the first cylindrical lens, e.g., Y', and the flat axis of the second cylindrical lens, e.g., Y".

The astigmatism compensation power is set by rotating the cylindrical lenses 140A, 140B with respect to one another. The astigmatism compensation power is greatest when the flat axes of the cylindrical lenses 140A, 140B are perpendicular to one another and least when the flat axes of the cylindrical lenses 140A, 140B are parallel to one another. If the cylindrical lens 140A, 140B have matched powers of opposite sign, the cylindrical lenses 140A, 140B will have no affect on the wavefront 10 when the flat axes of the cylindrical lenses are parallel.

In use, the astigmatism compensation device 104 of the illustrated embodiment receives the wavefront 10 along an optical axis 144. The wavefront 10 passes through the first cylindrical lens 140A and the second cylindrical lens 140B. Initially, both of the flat axes of the cylindrical lenses 140A, 140B are aligned with the bisector position 146 of the wavefront by their respective rotation motors 142A, 142B. The flat axis are aligned with one another so as not to add any astigmatism compensation to the wavefront 10. The motors 142A, 142B then rotate the flat axis of the cylindrical lenses 140A, 140B an equal amount in opposite directions from the bisector position 146 to add astigmatism compensation to the wavefront 10. The astigmatism compensation position and the astigmatism compensation power will be factored into the determination of aberrations of the wavefront 10 by the processor 27 of the wavefront compensation device 100.

As an illustrative example, if the bisector position 146 is at 45 degrees (FIG. 8B), the flat axes of the cylindrical lenses 140A, 140B (i.e, Y' in the plano-concave lens 140A depicted in FIG. 10A and Y" in the plano-convex lens 140B depicted in FIG. 10B) would be initially set at 45 degrees and, then, the first cylindrical lens 140A would be rotated to 60 degrees and the second cylindrical lens 140B would be rotated to 30 degrees to add astigmatism compensation. To add the maximum astigmatism compensation in the present example, the first cylindrical lens 140A would be rotated to 90 degrees and the second cylindrical lens 140B would be rotated to 0 degrees so that the flat axes of the first and second cylindrical lenses 140A and 140B would be perpendicular to one another.

For illustrative purposes, the present invention has been described in terms of measuring wavefront aberrations introduced by a human eye. However, it will be readily apparent to those skilled in the art that the present invention can be used to measure aberrations created by other optical systems, e.g. eyeglasses, telescopes, binoculars, monoculars, contact lenses, non-human eyes, or combination of these systems.

Having thus described a few particular embodiments of the invention, various alterations, modifications, and improvements will readily occur to those skilled in the art. For example, in alternative embodiments: the first cylindrical lens 140A is a converging lens and the second cylindrical lens 140B is a diverging lens; the flat surfaces of the plano-concave/convex lenses are facing one another; additional lens are used to fine tune the astigmatism compensation; the lenses are oriented relative to one another first and, then, the lenses are oriented relative to the wavefront 10; and the lenses are oriented relative to themselves and relative to one another substantially simultaneously. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. In an ophthalmic system for measuring eye aberrations having first and second optical lenses separated by a physical distance for focusing a wavefront, a method of adjusting the optical distance between the two lenses without changing the physical distance between the two lenses, the method comprising the following:
    (a) passing the wavefront through the first optical lens in a first optical path;
    (b) reflecting the wavefront from said first optical path to a second optical path different from said first optical path;
    (c) reflecting the wavefront to a third optical path different from said first and second optical paths; and
    (d) passing the wavefront through the second optical lens, and
    (e) reflecting the wavefront to a fourth optical path, said step being performed after step (c) and before step (d), wherein said first optical path and said fourth optical path are substantially collinear and steps (b) and (e) are performed by a single reflector device.

2. The method of claim 1 wherein said single reflector device is a prism.

3. The method of claim 2 wherein said second and third optical paths are a substantially same physical distance.

4. The ophthalmic system of claim 1, further including a method for correcting astigmatism, the astigmatism correction method comprising:
    (1) passing the wavefront through a cylindrical lens assembly having first and second cylindrical lens;
    (2) orienting the cylindrical lens assembly such that the astigmatism compensation position is in-line with the bisector position of the wavefront; and
    (3) orienting the first and second cylindrical lenses relative to one another to adjust the astigmatism compensation power of said cylindrical lens assembly.

5. The astigmatism correction method of claim 4 wherein steps 2 and 3 are performed separately.

6. In an ophthalmic system for measuring eye aberratons having first and second optical lenses separated by a physical distance for focusing a wavefront, a method of adjusting the optical distance between the two lenses without changing the physical distance between the two lenses, the method comprising the following:
    (a) passing the wavefront through the first optical lens in a first optical path;
    (b) reflecting the wavefront from said first optical path to a second optical path different from said first optical path;
    (c) reflecting the wavefront to a third optical path different from said first and second optical paths; and
    (d) passing the wavefront through the second optical lens wherein step (b) and step (c) are performed by a single reflector device and wherein the physical distances of the second and third optical paths are adjustable and wherein the physical distances of the second and third optical paths are adjustable by moving said single reflector device.

7. The method of claim 6 wherein said single reflector device is a retroreflector.

8. A method for removing astigmatism from a wavefront in an ophthalmic system for measuring eye aberrations, the method comprising the following:
    (a) passing the wavefront through a cylindrical lens assembly including a first cylindrical lens having a first axis and a second cylindrical lens having a second axis;
    (b) orienting said first axis of said first cylindrical lens and said second axis of said second cylindrical lens such that an astigmatism compensation position of said cylindrical lens assembly is in-line with a bisector position of the wavefront; and
    (c) orienting said first and second cylindrical lenses relative to one another to adjust the astigmatism compensation power of said cylindrical lens assembly.

9. The method of claim 8 wherein steps (b) and (c) are done substantially simultaneously.

10. The method of claim 8 wherein steps (b) and (c) are done separately.

11. The method of claim 10 wherein step (b) is done before step (c).

12. The method of claim 10 wherein step (c) is done before step (b).

13. In an ophthalmic system for measuring eye aberrations having first and second optical lenses separated by a physical distance for focusing a wavefront, an apparatus for adjusting the optical distance between the two lenses without changing the physical distance between the two lenses, the apparatus comprising:
    a first reflector positioned to reflect the wavefront received from the first lens along a first optical path to a second optical path, said second optical path being different from said first optical path;
    a second reflector positioned to reflect the wavefront from said second optical path to a third optical path, said third optical path being different from said first and second optical paths;

a third reflector positioned to reflect the wavefront from said third optical path to a fourth optical path which passes through the second optical lens and wherein said first optical path and said fourth optical path are substantially collinear and a single reflector device comprises at least said first reflector and said third refloctor.

14. The apparatus of claim 13 wherein said single reflector device is a prism.

15. The apparatus of claim 13 wherein said second reflector comprises a retroreflector.

16. The apparatus of claim 15 wherein said retroreflector is a comer cube.

17. The apparatus of claim 13, wherein said second and third optical paths are substantially a same physical distance.

18. The method of claim 17 wherein the physical distances of the second and third optical paths are adjustable.

19. The apparatus of claim 18 wherein the physical distances of the second and third optical paths is adjustable by moving said reflector.

20. The ophthalmic system of claim 13, further including an apparatus for correcting astigmatism, the astigmatism correction apparatus comprising:

a first cylindrical lens positioned within the path of the wavefront for introducing a first cylindrical refraction to the wavefront;

a second cylindrical lens positioned within the path of the wavefront for introducing a second cylindrical refraction to the wavefront;

said first and second cylindrical lenses mounted to be rotatable relative to the wavefront and relative to one another; and wherein the astigmatism compensation of said adjustable lens assembly is determined by the orientation of said first cylindrical lens and said second cylindrical lens relative to the wavefront and to one another.

21. The astigmatism correction apparatus of claim 20 further comprising:

a first rotation motor operably coupled to said first cylindrical lens for orienting said first cylindrical lens relative to the wavefront; and a second rotation motor operably coupled to said second cylindrical lens for orienting said second cylindrical lens relative to the wavefront.

22. In an ophthalmic system for measuring eye aberration, an apparatus for correcting astigmatism in a wavefront, said apparatus comprising:

a first cylindrical lens positioned within the path of the wavefront for introducing a first cylindrical refraction to the wavefront;

a second cylindrical lens positioned within the path of the wavefront for introducing a second cylindrical refraction to the wavefront;

said first and second cylindrical lenses mounted to be rotatable relative to the wavefront and relative to one another; and wherein the astigmatism compensation of said adjustable lens assembly is determined by the orientation of said first cylindrical lens and said second cylindrical lens relative to the wavefront and to one another.

23. The apparatus of claim 22 further comprising:

a first rotation motor operably coupled to said first cylindrical lens for orienting said first cylindrical lens relative to the wavefront; and a second rotation motor operably coupled to said second cylindrical lens for orienting said second cylindrical lens relative to the wavefront.

24. The apparatus of claim 23 wherein the first cylindrical lens and the second cylindrical lens are oriented in unison with respect to the wavefront such that the astigmatism compensation position of the apparatus can be brought in-line with the bisector position in the wavefront.

25. The apparatus of claim 23 wherein the first cylindrical lens and the second cylindrical lens are oriented relative to one another such that the magnitude of astigmatism correction cancels out astigmatism in the wavefront.

* * * * *

UNITED STATES PATENT AND TRADEMARK OFFICE
CERTIFICATE OF CORRECTION

PATENT NO. : 6,746,121 B2
DATED : June 8, 2004
INVENTOR(S) : Ross et al

It is certified that error appears in the above-identified patent and that said Letters Patent is hereby corrected as shown below:

Title page,
Item [76], Inventors, replace "Bjorne" with -- Bjoern --

Column 10,
Line 9, replace "aberatons" with -- aberrations --

Column 11,
Line 13, replace "comer" with -- corner --
Line 17, replace "are" with -- is --

Signed and Sealed this

Seventh Day of September, 2004

JON W. DUDAS
*Director of the United States Patent and Trademark Office*